United States Patent
Kuhr et al.

(12)

(10) Patent No.: US 6,409,740 B1
(45) Date of Patent: Jun. 25, 2002

(54) BLOOD LANCET SYSTEM FOR WITHDRAWING BLOOD FOR DIAGNOSTIC PURPOSES

(75) Inventors: Hans-Jurgen Kuhr, Mannheim; Herbert Argauer, Pirk, both of (DE)

(73) Assignee: Roche Diagnostics GmbH, Mannhein (DE)

( * ) Notice: Subject to any disclaimer, the term of this patent is extended or adjusted under 35 U.S.C. 154(b) by 19 days.

(21) Appl. No.: 09/677,726

(22) Filed: Oct. 2, 2000

(30) Foreign Application Priority Data

Oct. 9, 1999 (DE) .......................................... 199 48 759

(51) Int. Cl.⁷ .............................................. A61B 17/14
(52) U.S. Cl. ...................................................... 606/182
(58) Field of Search ............................ 606/1, 181, 185; 600/583

(56) References Cited

U.S. PATENT DOCUMENTS

| | | | |
|---|---|---|---|
| 4,924,879 A | 5/1990 | O'Brien | 128/770 |
| 5,035,704 A | * 7/1991 | Lambert et al. | 606/182 |
| 5,318,584 A | 6/1994 | Lange et al. | 606/182 |
| 5,951,582 A | * 9/1999 | Thorne et al. | 606/182 |

FOREIGN PATENT DOCUMENTS

EP  0458451 A1  11/1991

\* cited by examiner

*Primary Examiner*—George Manuel
(74) *Attorney, Agent, or Firm*—Richard T. Knauer; Jill L. Woodburn

(57) ABSTRACT

Blood lancet for withdrawing blood for diagnostic purposes. It has a housing with an outlet opening for the tip of a lancet, and a lancet drive with a drive rotor driven in a sense of rotation by a drive spring. The drive rotor converts the relaxation movement of the drive spring to a pricking movement, moving the lancet with high speed in pricking direction, until the tip protrudes from the outlet opening. The drive rotor has a pressure surface directed radially outwardly and running around the rotation axis with varying center distance. The pressure surface has a vertex with maximum center distance, and a propelling section, following the vertex against the sense of rotation and having a center distance decreasing against the sense of rotation. The drive spring effects a pressure on the propelling section of the pressure surface, thus driving the drive rotor in sense of rotation, whereas the drive rotor is coupled to the lancet holder.

28 Claims, 3 Drawing Sheets

BLOOD LANCET SYSTEM FOR WITHDRAWING BLOOD FOR DIAGNOSTIC PURPOSES

BACKGROUND AND SUMMARY OF THE INVENTION

The invention applies to a blood lancet device for withdrawing blood for diagnostic purposes. It comprises a housing with an outlet opening for the lancet tip, a lancet holder for holding the lancet and movable along a predetermined, straight puncturing path within the housing, and a lancet guide, guiding the lancet holder along the predetermined puncturing path.

In order to obtain a drop of blood, the blood lancet device must be pressed with a contact surface located around the outlet opening, against the skin (in particular against the finger tip or the earlobe). Subsequently, a pricking process is performed. During the pricking process, the lancet holder and the lancet held by it are moved along the predetermined puncturing path with high speed, driven by a lancet drive located in the blood lancet device, until the lancet tip comes out of the outlet opening and generates the wound necessary for obtaining the blood drop. After that, the lancet holder is driven back, by the lancet drive, into a position with the lancet tip inside the housing.

Lancet devices of this type are already known in many designs. In most cases, the lancet drive is a simple mechanism driving the lancet holder directly by a linear spring, being stopped by a thrust block at the point of the longest protrusion of the lancet tip. This stops the lancet abruptly; the spring action returns the lancet into its initial position. Such a blood lancet device can be produced simply. It is, however, not optimal with respect to its function, in particular as the pain caused by the prick is relatively high.

However, reduction of the pain caused by wound generation is of high medical importance. This is particularly true for diabetics, who must control their glucose level frequently and regularly, in order to adapt the necessary insulin injections to their requirements (depending on factors as e.g. food ingestion, physical activity and others), thus, if possible, always keeping the glucose level within defined target limits. This is of highest importance for the health of those patients, especially for the avoidance of serious late injuries, as e.g. amaurosis. Comprehensive investigations have shown that a tight glucose level control can dramatically reduce serious late injuries caused by diabetes mellitus.

Blood lancet devices which convert the relaxation movement of the drive spring by means of a rotatable drive rotor into the prick movement allow blood withdrawal with little pain. The vibration caused by the impact of the lancet holder onto a thrust block can be avoided.

U.S. Pat. No. 4,924,879 describes a blood lancet device with a rotor drive of that type, driving the rotor by a coaxial coil spring. The rotation movement of the rotor is converted to the linear movement of the lancet by means of a push rod system.

In the lancet device described in U.S. Pat. No. 5,318,584, the drive rotor has a rotation axis parallel to the prick direction. Here, it is also driven by a coaxial coil spring. The conversion of the rotational movement into the necessary linear movement of the lancet holder is performed by a rotary drive, preferably realized by a cam control. In this mechanism, a pivot of the lancet holder meshes with a corresponding recess in the rotor. This design allows a very good pricking behavior with low vibrations and a precisely reproducible pricking depth. This makes the pain, occurring with the wound generation, very small. However, a disadvantage of this system is the necessity of components with relatively complex shape which have to interact in a very precise way. Thus, their production is expensive. A precise manufacturing is the condition for a reliable function.

Based on this, the invention addresses the problem to provide a blood lancet device which achieves a pricking behavior which is low in vibrations and precise, and which can be produced with less manufacturing expense, thus reducing production costs.

With a blood lancet device of the type described above, with a rotor driven lancet holder, this task is obtained in the following way: The drive rotor has a pressure surface which is directed radially outwardly and runs with varying center distance around the rotation axis in such a manner that it has a vertex with maximum center distance, and a propelling section following the vertex against the sense of rotation, with a center distance decreasing against the sense of rotation. The drive spring is adapted for effecting in a propelling angle section of the rotation of the drive rotor via a pressure element a pressure with a component in radial direction to the rotation axis onto the propelling section of the pressure surface, thus driving the drive rotor by the pressure of the drive spring onto the pressure surface in the propelling section in the sense of rotation. The drive rotor is coupled via an output-side coupling mechanism with the lancet holder, in such a manner that the tip of the lancet protrudes from the outlet opening at a point of time in which the drive rotor is in the propelling angle section.

The drive rotor having a pressure surface which is directed in radially outward direction (away from the rotation axis) can be easily produced as a plastic part. The power transmission from the drive spring to the rotation movement of the drive rotor (subsequently called "drive-side coupling mechanism of the lancet drive") is determined by the form of the drive section of the pressure surface. Thus, different required drive rotor movement characteristics (rotation speed depending on rotation angle) can be adjusted by different designs of the pressure surface. A form with a propelling section which is, at least in parts of the propelling section, convex, has proven advantageous.

For tensioning, the drive rotor must be moved into a position where the pressure element is in contact with the pressure surface at the vertex. This can be obtained with different tensioning mechanisms. Preferably, not only the prick movement drive, but also the tensioning of the lancet drive is realized by an interaction of the spring and the pressure surface. To this end the pressure surface has a tensioning section with a center distance from the rotor center which increases against the sense of rotation. The tensioning section, too, has a convex shape, at least in a partial section thereof.

According to another preferred design, the output-side coupling mechanism, which converts the rotation movement of the drive rotor to the pricking and retraction movement of the lancet holder, is formed by a recess rotatable with the drive rotor, forming an operating cam and meshing with a pivot connected to the lancet holder. This design allows a variation of the output-side coupling mechanism, according to the desired pricking behavior, a corresponding variation of the form of the operating cam. This results in comprehensive possibilities for optimization of the speed profile of the pricking movement (dependence of current speed from lancet holder position) with respect to a pain which is as low as possible. A particularly simple design is obtained if the recess forming the operating cam is located in the drive rotor.

BRIEF DESCRIPTION OF THE DRAWINGS

The invention will subsequently be further explained with the design examples represented in the figures. The details described therein can be applied individually or in combination with each other in order to obtain preferred embodiments of this invention.

DETAILED DESCRIPTION OF THE INVENTION

Figure 1:
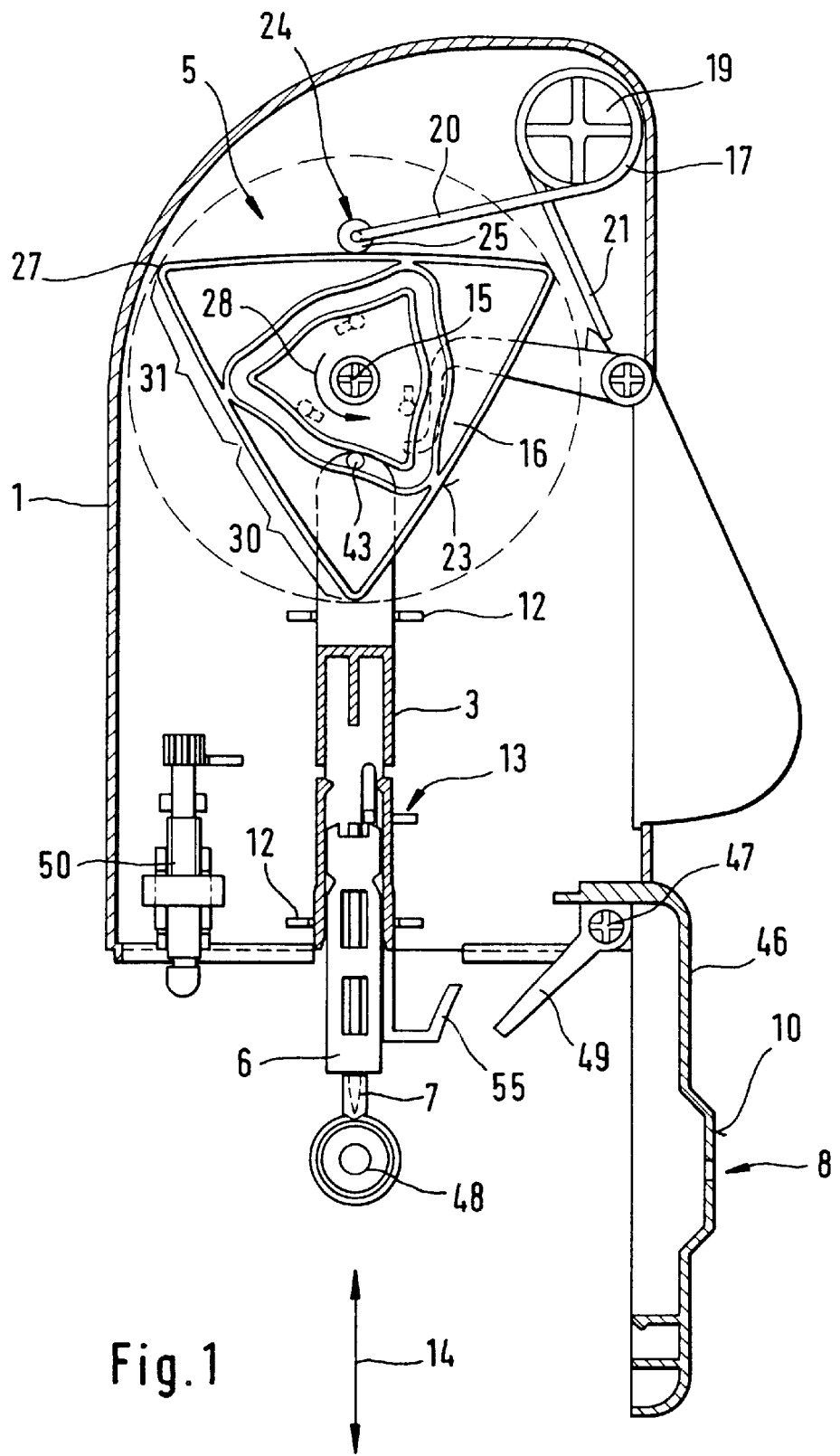
FIG. 1 shows a longitudinal section through a blood lancet device according to the invention in a position in which a lancet is inserted into the lancet holder.
Figure 3:
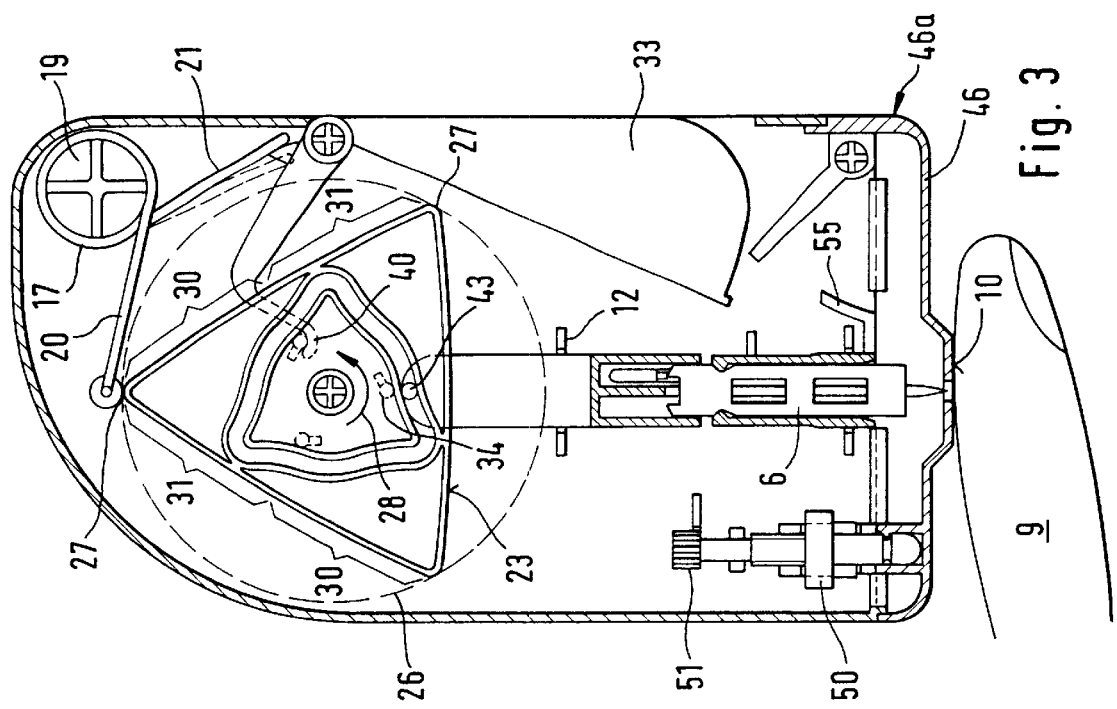
FIG. 3 shows a longitudinal section through the device according to FIG. 1 in the tensioned position of the lancet drive.
Figure 2:
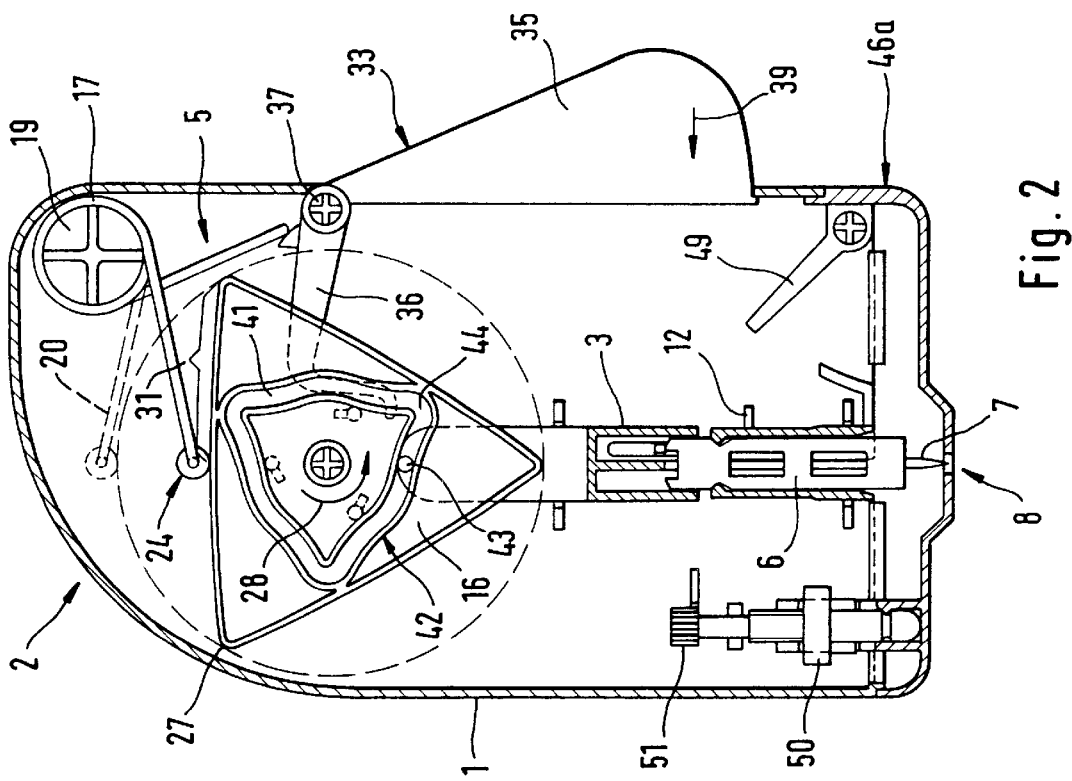
FIG. 2 shows a longitudinal section through the device according to FIG. 1, in the rest position of the lancet drive.

In the housing 1 of the blood lancet device 2 represented in FIGS. 1 to 3, a lancet holder 3 is driven by a lancet drive, in its entirety designated with 5, in a way that a lancet 6 fixed in the lancet holder 3 performs a pricking movement during which the tip 7 protrudes out of an outlet opening 8 of the housing 1, in order to generate a wound at a body part 9 which is in contact with the outlet opening 8 (FIG. 3). The surface surrounding the outlet opening, designed for contacting the body part 9, is designated as the contact surface 10. In the case represented, the pricking and retraction movement of the lancet holder 3 is precisely guided by a lancet guide 13, formed by plastic bridges 12, on a linear and straight puncturing path, such that practically no vibrations with movement components vertical to the pricking direction, which is symbolized in FIG. 1 by arrow 14, can arise.

The lancet drive 5 consists essentially of a drive rotor 16 rotating on an axis 15, and a drive spring 17, designed in the represented case as a coil spring with two legs 20, 21 and coiled around a fixing post 19.

The drive rotor 16 presents a radially outwardly directed pressure surface 23 which runs around the rotation axis 15 in varying distance therefrom. The first leg 20 of the drive spring 17 effects a force, via a pressure element 24, with a component in radial direction towards the rotation axis 15, onto the pressure surface 23. This pressure transmission should be as low friction as possible. Therefore, the pressure element 24 is designed as a wheel 25, fixed at the end of the first leg 20, running on the pressure surface 23. The second leg 21 is fixed outside the rotation range 26 of the drive rotor 16.

The drive rotor 16 is triple-symmetric with axis 15 as center of symmetry, so that its shape elements are repeated every 120°.

In the drawing plane of FIGS. 1 to 3, which corresponds to the rotation plane of drive rotor 16, the pressure surface 23 is approximately triangular. The (slightly rounded) corners form vertexes 27, delimiting the maximum distance of pressure surface 23 from the rotation axis 15. The vertexes are followed, against the sense of rotation (marked by arrow 28) of the drive rotor 16, by a section with decreasing center distance, called propelling section 30. In front of the vertexes 27 (referring to the sense of rotation 28) there are respective sections of the pressure surface 23, the center distance of which decreases in sense of rotation (thus increasing against the sense of rotation), and which are called tensioning sections 31. As a whole, the pressure surface 23 has a slight convex curvature in the rotation plane between the vertexes 27.

In order to tension the lancet drive 5, the lancet rotor 16 must be rotated, in the sense of rotation 28, from the rest position shown in FIG. 2, to the tensioned position shown in FIG. 3. This can be effected, e.g., by an electric rotor drive. However, a mechanic tensioning device is preferred. In the represented case, the tensioning device has a tensioning lever 33, which effects a torque, in sense of rotation 28, onto a thrust piece 34 (in the represented case formed by a cylindrical pin) mounted on the drive rotor and protruding from the front surface of the rotor 16. The tensioning lever 33 consists on an actuator key 35 protruding in rest position (FIG. 2) laterally from the housing 1, and a swiveling arm 36 located inside the housing 1. Between the actuator key 35 and the swiveling arm 36 there is a pivot bearing 37, the axis of which is parallel to the rotation axis 15 of the drive rotor 16. For tensioning the lancet drive 5, the actuator key 35 must be pressed into the housing in direction of arrow 39. This makes the swiveling arm swivel upwards, and a hook 40 located at the end of the swiveling arm 36 catches one of the thrust pieces 34, thus rotating the rotor 16 in sense of rotation 28. Thereby pressure element 24 moves along a tensioning section 31 of the pressure surface 23. The distance of the pressure element 24 from the rotation axis 15 increases, whereas the drive spring 17 is increasingly tensioned, until its first leg 20 reaches a position (represented in dotted line in FIG. 2) with maximum distance from rotation axis 15. Once the lancet drive 5 is completely tensioned, the drive rotor 16 is located in the position represented in FIG. 3, where the pressure element 24 is pressing against a vertex 27 of pressure surface 23.

As soon as the lancet rotor 16 is further rotated in sense of rotation 28, the pressure element 24 enters into the propelling section 30 of the pressure surface 23. With this, an angle section of the movement of the drive rotor begins, in which the pressure of drive spring 17 (generally directed towards rotation axis 15, at least having a component in that direction) is converted to a torque driving the drive rotor 16 in sense of rotation 28. This angle section, where the pressure element 24 is in contact with the propelling section 30, is called propelling angle section.

Drive spring 17 with pressure element 24 and pressure surface 23 form a drive-side coupling mechanism, which generates a rotation movement of the drive rotor 16 which takes place with high speed and automatically in the propelling angle section (in this movement phase it is neither possible nor necessary for the user to intervene). In order to convert this rotation movement into the necessary linear movement of the lancet holder with lancet 6, an output coupling mechanism is necessary, which can be realized in different ways. E.g. a push rod mechanism, as shown in U.S. Pat. No. 4,924,879, is appropriate.

However, the design shown in the figures is preferred. It features an operating cam 42, formed by a recess 41, preferably integrated into the drive rotor 16, rotating commonly with the drive rotor 16. A pivot 43 connected to the lancet holder 3 meshes with the operating cam in a way that at least a part of the pricking and retraction movement is controlled by the rotation of the operating cam 42 in relation to the pivot. To this end, the pivot moves along the operating cam 42. The maximum deflection of the lancet holder 3 in pricking direction is determined by a lower reverse point 44 of the operating cam 42, located in such a position that the pivot 43 moves through the lower reverse point within the propelling angle section of the rotor movement. The pivot is preferably fixed directly to the lancet holder 3 (at the end opposite to the lancet tip 7).

In order to facilitate the insertion of a lancet 6 into the lancet holder 3, there is an end piece 46 provided at the lower end of the housing 1, having an oblong form with a main axis parallel to the rotor level (i.e. in the drawing plane of FIGS. 1 to 3). It is fixed to the housing and can be swiveled to one side about one of its short sides 46a (by means of a hinge 47 with swiveling axis parallel to the rotor axis). For lancet insertion, the lower end of the housing (1) must be opened by swiveling the end piece 46 (FIG. 1) aside, so that the lancet holder becomes accessible. The lancet is taken by its protection cap 48 covering its tip 7, and pushed into the lancet holder 3. Further details about appropriate lancet holders can be taken from the U.S. Pat. No. 5,318,584 and the publications cited therein.

The end piece 46 is coupled to a swiveling arm 49, which collides with a bracket 55 when the lower end piece 46 is opened. Bracket 55 and lancet holder 3 interact in a way that an inserted lancet will be automatically thrown out of lancet holder 3, due to the collision with swiveling arm 49, when the end piece 46 is opened.

An adjusting device 50 for adjusting the pricking depth is located at the short side of the end piece 46, opposite from the hinge 47. It allows the adjustment of the distance (in pricking direction) between end piece 46 and the housing 1. The longer that distance is, the smaller becomes with unchanged movement path of the lancet holder 3 the pricking depth. A knurled screw 51 is provided for adjusting the adjusting device 50. It is accessible from the outside through a recess in the housing wall (not represented).

Figure 4:
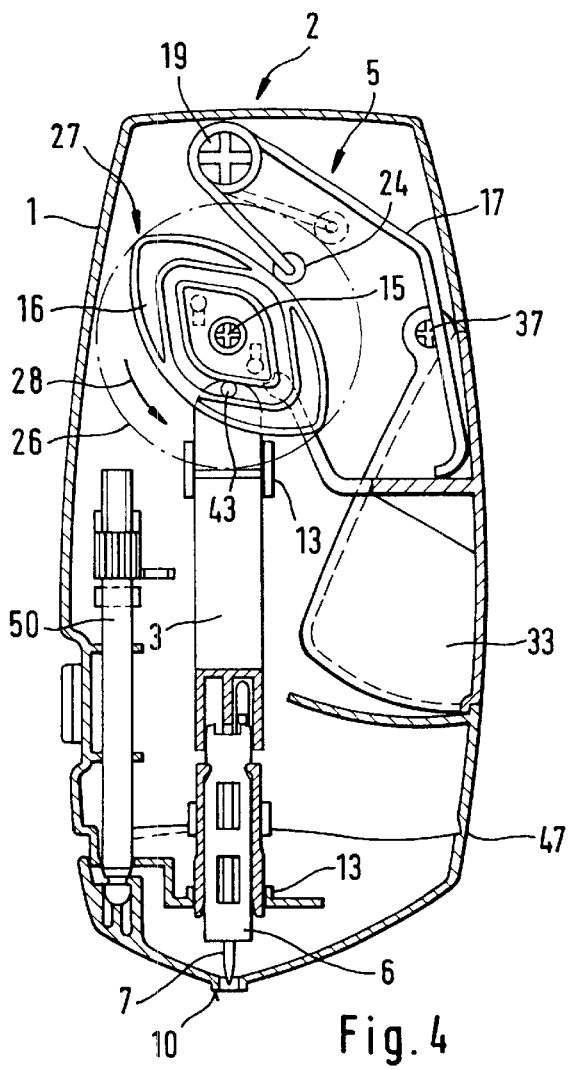
FIG. 4 shows a longitudinal section through an alternative design of a blood lancet device in rest position.
Figure 5:
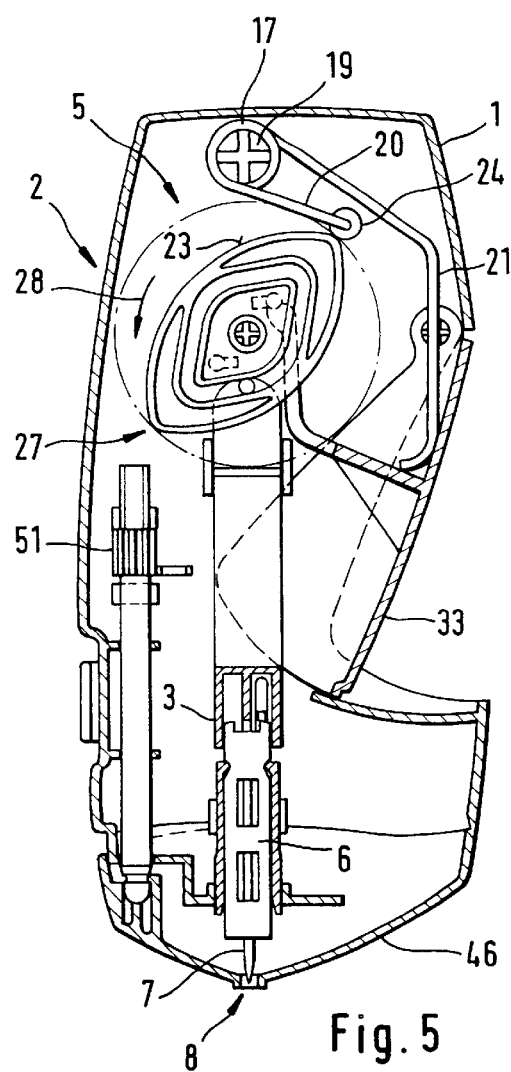
FIG. 5 shows a longitudinal section through the device according to FIG. 4 in the tensioned position of the lancet drive.

The design represented in FIGS. 4 and 5 has a housing more sleek and compact than the lancet device represented in FIGS. 1 to 3. It corresponds, however, to the latter with respect to most technical characteristics. Components with the same function are identified by the same numerals.

A special characteristic of this design is the double-symmetric form of the drive rotor 16. Its pressure surface 23, thus, has two vertexes 27 with correspondingly adjacent propelling and tensioning sections 30 and 31. This allows a smaller design. The rotor 16 can be kept particularly small, if the position of the pressure element 24 is shifted laterally from the longitudinal axis of lancet holder 3. By this, the operating cam can be oriented in a way that its lower reverse points, with respect to the rotation axis 15, are oriented approximately in the same direction as the vertexes 27 of the pressure surface 23. At the same time, the condition that the pivot 43 moves along the lower reverse point 44 within the propelling angle section of the drive rotor movement, is complied with.

Figure 6:
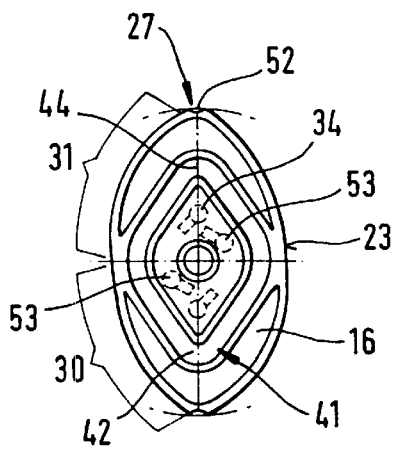
FIG. 6 shows a lateral view of the drive rotor of the device according to FIG. 4
Figure 7:
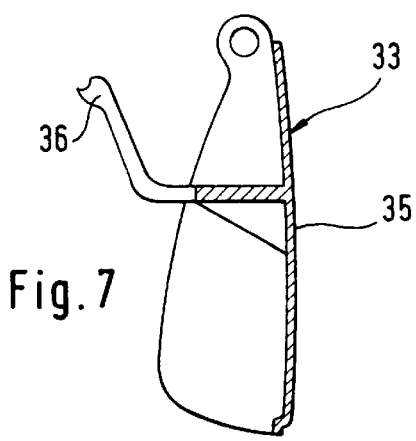
FIG. 7 shows a lateral view of the tensioning lever of the device according to FIG. 4.

A further special characteristic of the design represented in FIGS. 4 and 5 becomes apparent from the separate representation of the components in FIGS. 6 and 7. In FIGS. 1 to 3 the pressure surface 23 has a continuous convex bow in the vicinity of the vertexes 27, so that the tensioning movement passes, without stop, to the propelling movement of the drive rotor 16, once the tensioning lever 33 is operated. The drive rotor represented in FIG. 6, however, has a small recess 52 at the vertexes 27, the shape of which makes the pressure element 24 latch into it. In order to trigger the transition towards the propelling angle section of rotor movement 16, and thus the pricking movement, an additional triggering mechanism is provided. In the represented case, it is realized by two additional thrust pieces 53 of the drive rotor 16, and a special shape of the swiveling arm 36 of the tensioning lever 33. These elements are matched in a way that the meshing of the swiveling arm 36 and the thrust piece 34 is interrupted in the moment when the pressure element 24 latches into recess 52. By a short release and new actuation of key 35, the swiveling arm 36 meshes again with one of the additional thrust pieces 53. This triggers the pricking movement.

Numerous further designs of this invention are possible. The drive rotor is preferably N-symmetric (N=2,3,4). Generally, a non-symmetrical design is possible, too. In particular, a drive rotor with only one vertex and a cam-shaped form of the pressure surface 23 can be applied. The pressure surface is preferably a continuous surface completely surrounding the axis. However, it may be interrupted if other constructive measures assure that the drive rotor reaches a state where the pressure element 24 approaches a vertex 27, followed by a propelling section with the described characteristics. Generally, the pressure surface 23 is a surface generated by the movement of a straight line in space (ruled surface), with the generating line proceeding parallel to the axis of the drive rotor. However, a certain inclination or bending of the pressure surface 23 is possible, too, if the functions described herein are not impaired thereby.

This invention combines the advantages of a simple and robust mechanical system with a highly precise lancet guide. It can be realized with few components and allows simple assembly. Most parts are made of plastic and can be cheaply produced in large quantities, in particular in die-cast technology. The drive spring consists of spring steel and has a simple geometry, allowing a cheap production, too.

We claim:

1. Blood lancet device for withdrawing blood from a body part for diagnostic purposes, comprising
    a housing with an outlet opening for a tip of a lancet and a contact surface around the outlet opening for contacting to the body part,
    a lancet holder for holding the lancet and movable within the housing along a predetermined puncturing path,
    a lancet guide guiding the lancet holder along the predetermined puncturing path,
    a lancet drive with a drive rotor driven by a drive spring in a sense of rotation, by which lancet drive a relaxation movement of the drive spring is converted into a pricking movement during which the lancet held by the lancet holder moves with high speed along the predetermined puncturing path in a pricking direction, until its tip protrudes from the outlet opening and a wound is generated at the body part contacting the contact surface and by which lancet drive the lancet holder is retracted to a position where the tip of the lancet is within the housing,
    wherein
        the drive rotor has a pressure surface which is directed radially outwardly and runs with varying center distance around the rotation axis in such a manner that it has a vertex with maximum center distance, and a propelling section following the vertex against the sense of rotation, with a center distance decreasing against the sense of rotation, the drive spring is adapted for effecting in a propelling angle section of the rotation of the drive rotor via a pressure element a pressure with a component in radial direction to the rotation axis onto the propelling section of the pressure surface, thus driving the drive rotor by the pressure of the drive spring onto the pressure surface in the propelling section in the sense of rotation, and the drive rotor is coupled via an output-side coupling mechanism with the lancet holder, in such a manner that the tip of the lancet protrudes from the outlet opening at a point of time in which the drive rotor is in the propelling angle section.

2. Blood lancet device according to claim 1, wherein the propelling section has a convex shape in at least a partial section thereof.

3. Blood lancet device according to claim 1, wherein the pressure surface comprises a tensioning section preceding the vertex against the sense of rotation, and having an increasing center distance against the sense of rotation.

4. Blood lancet device according to claim 3, wherein the tensioning section has a convex shape in at least a partial section thereof.

5. Blood lancet device according to claim 3, wherein the pressure surface has in its range adjacent the vertex a continuous convex shape, so that the tensioning movement passes to the pricking movement without a stop.

6. Blood lancet device according to claim 3, wherein the pressure surface has a recess at the vertex, where the pressure element latches in.

7. Blood lancet device according to claim 1, wherein the pressure surface has at least two vertexes.

8. Blood lancet device according to claim 1, wherein the pressure surface is a continuous surface completely surrounding the axis.

9. Blood lancet device according to claim 1, wherein the output-side coupling mechanism includes a recess, rotatable together with the drive rotor, and forming an operating cam, in mesh with a pivot linked to the lancet holder, where at least a part of the pricking and retraction movement is determined by a rotation movement of the operating cam, where the pivot moves along the operating cam formed by the recess, and where the maximum deflection of the lancet holder in pricking direction is determined by a lower reverse point in the operating cam.

10. Blood lancet device according to claim 9, wherein the recess which forms the operating cam is formed in the drive rotor.

11. Blood lancet device according to claim 1, comprising a tensioning lever which effects a torque in the sense of rotation onto a thrust piece provided on the drive rotor, for the tensioning of the lancet drive.

12. Blood lancet device according to claim 1, wherein the housing has an end piece with the contact surface, having an elongated shape, the main axis of which is parallel to the rotor plane, and which is articulated to the housing on one of its shorter sides, with a hinge.

13. Blood lancet device according to claim 12, wherein the end piece is provided with an adjusting device at the shorter side opposite to the hinge, for the adjustment of the distance from the housing and thus for adjusting the pricking depth.

14. A blood lancet device comprising:
a lancet including a tip,
a housing including an outlet opening for the tip and a contact surface around the outlet opening,
a lancet holder being movable in the housing along a path,
a lancet guide formed to guide the lancet holder along the path,
a pressure element,
a lancet drive including a rotor driven by a spring in a sense of rotation, the rotor having a pressure surface extending about a rotation axis and being formed to contact the pressure element, the pressure surface running with varying center distance around the rotation axis and having a vertex with a maximum center distance from the rotation axis and a propelling section following the vertex against the sense of rotation with a center distance decreasing against the sense of rotation and the spring acting onto the pressure element to effect a pressure against the propelling section of the pressure surface with a component in a radial direction to the rotation axis to drive rotation of the pressure surface about the rotation axis, and
an output-side coupling mechanism coupling the rotor with the lancet holder so that movement of the pressure element across the propelling section is converted into movement of the lancet holder along the path in a pricking direction.

15. A blood lancet device comprising:
a lancet including a tip,
a housing including an outlet opening for the tip and a contact surface around the outlet opening,
a lancet holder being movable in the housing along a path,
a lancet guide formed to guide the lancet holder along the path,
a pressure element,
a lancet drive including a rotor driven by a spring in a sense of rotation, the rotor having a pressure surface extending about a rotation axis and being formed to contact the pressure element, the pressure surface having a vertex with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, the propelling section having a convex shape in at least a partial section thereof, and
an output-side coupling mechanism coupling the rotor with the lancet holder so that movement of the pressure element across the propelling section is converted into movement of the lancet holder along the path in a pricking direction.

16. A blood lancet device comprising:
a lancet including a tip,
a housing including an outlet opening for the tip and a contact surface around the outlet opening,
a lancet holder being movable in the housing along a path,
a lancet guide formed to guide the lancet holder along the path,
a pressure element,
a lancet drive including a rotor driven by a spring in a sense of rotation, the rotor having a pressure surface extending about a rotation axis and being formed to contact the pressure element, the pressure surface having a vertex with a maximum center distance from the rotation axis and comprising a tensioning section preceding the vertex against the sense of rotation, the tensioning section having an increasing center distance against the sense of rotation and a propelling section following the vertex against the sense of rotation and the spring acting onto the pressure element to effect a pressure against the propelling section of the pressure surface with a component in a radial direction to the rotation axis to drive rotation of the pressure surface about the rotation axis, and an output-side coupling mechanism coupling the rotor with the lancet holder so that movement of the pressure element across the propelling section is converted into movement of the lancet holder along the path in a pricking direction.

17. Blood lancet device according to claim 16 wherein the propelling section has a decreasing center distance against the sense of rotation.

18. Blood lancet device according to claim 16 wherein the tensioning section has a convex shape in at least a partial section thereof.

19. Blood lancet device according to claim 16 wherein the pressure surface has in its range adjacent the vertex a continuous convex shape.

20. Blood lancet device according to claim 16 wherein the pressure surface has a recess at the vertex.

21. A blood lancet device comprising:

a lancet including a tip, a housing including an outlet opening for the tip and a contact surface around the outlet opening, a lancet holder being movable in the housing along a path, a lancet guide formed to guide the lancet holder along the path, a pressure element, a lancet drive including a rotor driven by a spring in a sense of rotation, the rotor having a pressure surface extending about a rotation axis and being formed to contact the pressure element, the pressure surface having at least two vertexes with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, and an output-side coupling mechanism coupling the rotor with the lancet holder so that movement of the pressure element across the propelling section is converted into movement of the lancet holder along the path in a pricking direction.

22. A blood lancet device comprising:

a lancet including a tip, a housing including an outlet opening for the tip and a contact surface around the outlet opening, a lancet holder being movable in the housing along a path, a lancet guide formed to guide the lancet holder along the path, a pressure element, a lancet drive including a rotor driven by a spring in a sense of rotation, the rotor having a pressure surface extending about a rotation axis and being formed to contact the pressure element, the pressure surface being a continuous surface completely surrounding the axis and having a vertex with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, and an output-side coupling mechanism coupling the rotor with the lancet holder so that movement of the pressure element across the propelling section is converted into movement of the lancet holder along the path in a pricking direction.

23. A blood lancet device comprising:

a lancet including a tip, a housing including an outlet opening for the tip and a contact surface around the outlet opening, a lancet holder being movable in the housing along a path and including a pivot, a lancet guide formed to guide the lancet holder along the path, a pressure element, a lancet drive including a rotor driven by a spring in a sense of rotation, the rotor having a pressure surface extending about a rotation axis and being formed to contact the pressure element, the pressure surface having a vertex with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, and an output-side coupling mechanism coupling the rotor with the lancet holder so that movement of the pressure element across the propelling section is converted into movement of the lancet holder along the path in a pricking direction and including an operating cam in mesh with the pivot, so that at least a part of the pricking and retraction movement is determined by a rotation movement of the operating cam.

24. Blood lancet device according to claim 23 wherein the operating cam includes a lower reverse point and a maximum deflection of the lancet holder in the pricking direction is determined by the lower reverse point.

25. Blood lancet device according to claim 23 wherein the operating cam is formed in the rotor.

26. A blood lancet device comprising:

a lancet including a tip, a housing including an outlet opening for the tip and a contact surface around the outlet opening, a lancet holder being movable in the housing along a path, a lancet guide formed to guide the lancet holder along the path, a pressure element, a lancet drive including a rotor driven by a spring in a sense of rotation, the rotor including a thrust piece and having a pressure surface extending about a rotation axis and being formed to contact the pressure element, the pressure surface having a vertex with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, a tensioning lever formed to effect a torque in the sense of rotation onto the thrust piece, and an output-side coupling mechanism coupling the rotor with the lancet holder so that movement of the pressure element across the propelling section is converted into movement of the lancet holder along the path in a pricking direction.

27. A blood lancet device comprising:

a lancet including a tip, a housing including an outlet opening for the tip, a contact surface around the outlet opening, a lower end and an end piece that is articulated to the lower end of the housing with a hinge, a lancet holder being movable in the housing along a path, a lancet guide formed to guide the lancet holder along the path, a pressure element, a lancet drive including a rotor driven by a spring in a sense of rotation, the rotor having a pressure surface extending about a rotation axis and being formed to contact the pressure element, the pressure surface having a vertex with a maximum center distance from the rotation axis and a propelling section following the vertex against the sense of rotation and the spring acting onto the pressure element to effect a pressure against the propelling section of the pressure surface with a component in a radial direction to the rotation axis to drive rotation of the pressure surface about the rotation axis, and an output-side coupling mechanism coupling the rotor with the lancet holder so that movement of the pressure element across the propelling section is converted into movement of the lancet holder along the path in a pricking direction.

28. Blood lancet device according to claim 27 wherein the end piece is provided with an adjusting device that is formed to move the distance of the end piece from the lower end of the housing.

* * * * *